(12) United States Patent
Blaufelder et al.

(10) Patent No.: US 6,624,327 B1
(45) Date of Patent: Sep. 23, 2003

(54) PROCESS FOR PREPARING BETAINES

(75) Inventors: Christian Blaufelder, Wuppertal (DE); Reinhard Broucek, Wuppertal (DE); Axel Carstens, Wuppertal (DE); Ludwig Eisenhuth, Wuppertal (DE)

(73) Assignee: Akzo Nobel N.V., Arnhem (NL)

( * ) Notice: Subject to any disclaimer, the term of this patent is extended or adjusted under 35 U.S.C. 154(b) by 0 days.

(21) Appl. No.: 10/048,876

(22) PCT Filed: Jul. 6, 2000

(86) PCT No.: PCT/EP00/06452
§ 371 (c)(1),
(2), (4) Date: May 2, 2002

(87) PCT Pub. No.: WO01/10818
PCT Pub. Date: Feb. 15, 2001

(30) Foreign Application Priority Data

Aug. 6, 1999 (EP) .............................................. 99202584

(51) Int. Cl.$^7$ ............................................ C07C 229/00
(52) U.S. Cl. ........................................ 562/575; 562/526
(58) Field of Search ................................. 562/575, 526

(56) References Cited

U.S. PATENT DOCUMENTS 5,895,823 A * 4/1999 Ramprasad et al.
6,046,356 A * 4/2000 Ramprasad et al.

* cited by examiner

Primary Examiner—Michael L. Shippen
(74) Attorney, Agent, or Firm—Richard P. Fennelly

(57) ABSTRACT

The invention relates to a process for preparing betaines of formula (I) wherein $R^1$ represents a $C_1$–$C_{24}$ hydrocarbon group, and $R^2$ and $R^3$ independently represent a $C_1$–$C_3$ hydrocarbon group, comprising reacting an aqueous solution of an ethoxylated quaternay ammonium compound of formula (II) wherein $R^1$, $R^2$, and $R^3$ have the same meaning as described above and $X^-$ represents a suitable anion, with oxygen or an oxygen-containing gas under alkaline conditions in the presence of a supported and promoted Pt catalyst at a temperature ranging from room temperature to 70° C. Preferably, use is made of a Pt/Bi/C catalyst. The invention process is particularly suitable for converting choline chloride into betaine, which is used as an animal feed

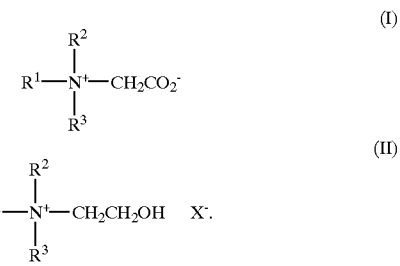

9 Claims, No Drawings

PROCESS FOR PREPARING BETAINES

This application is a national phase filing of PCT International Patent Application No. PCT/EP00/06452, filed on Jul. 6, 2000, which claims priority from European Patent Application No. 99202584.1, filed on Aug. 6, 1999.

The invention relates to a process for preparing betaines.

Betaines are surfactants which are of value in personal care products, e.g., as a skin cleanser, and as an animal feed.

Several processes for preparing betaines are known in the art including alkylation and oxidation procedures.

U.S. Pat. No. 5,895,823 discloses a process for preparing aqueous solutions of betaines by reacting an aqueous solution of a choline salt, particularly choline hydroxide, with oxygen in the presence of a supported noble metal catalyst at a temperature of 20 to 100° C. The best results in terms of choline conversion and betaine selectivity are obtained by sparging oxygen through an aqueous solution of choline hydroxide at 78° C. for 5.5 h using 5% Pd/C as the catalyst, i.e. Example 5 of U.S. Pat. No. 5,895,823.

Disadvantages of the process of U.S. Pat. No. 5,895,823 are that the choline conversion and the betaine selectivity are both relatively low and the reaction is carried out for a prolonged period of time at a relatively high temperature, leading to a low space-time yield. Furthermore, a relatively high amount of catalyst is used. All in all, the process of U.S. Pat. No. 5,895,823 is unattractive for carrying out on a technical scale in an economical way.

An important parameter for a process employing a noble metal catalyst which is to be carried out on an industrial scale is the stability of the catalyst, i.e., the loss of precious noble metal leading to a decrease in catalytic activity, and related to that the recyclability of the catalyst. It was found that the 5% Pt/C catalyst exemplified in Examples 1 and 2 of U.S. Pat. No. 5,895,823 has poor stability/recyclability.

Hence, for all of the above-mentioned reasons there is a need in the art for an improved process for preparing betaines.

Surprisingly, we have found a process which does not suffer from the aforementioned disadvantages and in which the noble metal catalyst can be reused many times without showing a significant loss of noble metal.

The process of the present invention is a process for preparing betaines of formula I:

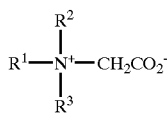
I wherein $R^1$ represents a $C_1$–$C_{24}$ hydrocarbon group, and $R^2$ and $R^3$ independently represent a $C_1$–$C_3$ hydrocarbon group, comprising reacting an aqueous solution of an ethoxylated quaternary ammonium compound of formula II:

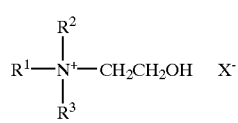
II wherein $R^1$, $R^2$, and $R^3$ have the same meaning as described above and $X^-$ represents a suitable anion, with oxygen or an oxygen-containing gas under alkaline conditions in the presence of a supported and promoted Pt catalyst at a temperature ranging from room temperature to 70° C.

$R^1$ may be a linear or branched, saturated or unsaturated $C_1$–$C_{24}$ hydrocarbon group. $R^2$ and $R^3$ independently may be a linear or branched $C_1$–$C_3$ hydrocarbon group. Preferably, $R^1$ is a $C_1$–$C_{22}$, more preferably $C_1$–$C_{18}$, most preferably $C_1$–$C_3$ hydrocarbon group. $R^2$ and $R^3$ preferably are methyl or ethyl, most preferably methyl groups. Typical examples of $R^1$ groups include methyl, ethyl, hexyl, octyl, decyl, dodecyl, oleyl, coco, and tallow groups.

Preferred compounds of formula II are compounds in which $R^1$ represents a $C_1$–$C_{24}$ hydrocarbon group and $R^2$ and $R^3$ represent methyl groups. Particularly preferred compounds of formula II are the so-called choline salts, in which $R^1$–$R^3$ represent methyl groups.

The $X^-$ group may be any anion and it typically results from the method that is chosen to prepare the ethoxylated quaternary ammonium compound of formula II. For example, it may result from the quaternization of the corresponding tertiary amine with a hydrocarbyl halide such as methyl chloride, methyl iodide, allyl chloride, and 2-chloroethanol, or a dihydrocarbyl sulfate such as dimethyl sulfate and diethyl sulfate. For example, choline chloride can be obtained by the reaction of trimethylamine with 2-chloroethanol. However, choline chloride can also be obtained by the reaction of trimethylamine hydrochloric acid salt with ethylene oxide. Alternatively, the anion may result from an anion-exchange reaction, e.g., by converting choline chloride into choline hydroxide.

Suitable ethoxylated tertiary amines and quaternization procedures leading to the starting materials of the process of the present invention as well as the exchange reactions mentioned above are well-known to one of ordinary skill in the art.

Preferably, the anion is a halide ion, most preferably a chloride ion.

Typical examples of compounds of formula II include choline salts such as choline chloride, choline dihydrogen citrate, tricholine citrate, choline bitartrate, choline acetate, choline phosphate, choline sulfate, choline carbonate, choline bicarbonate, and choline hydroxide, N-coco N,N-dimethyl N-(2-hydroxyethyl) ammonium chloride, N-tallow N,N-dimethyl N-(2-hydroxyethyl) ammonium chloride, N-dodecyl N,N-dimethyl N-(2-hydroxyethyl) ammonium chloride, and N-oleyl N,N-dimethyl N-(2-hydroxyethyl) ammonium chloride.

A particularly preferred starting material is choline chloride, which is, e.g., commercially available in the solid form (99% and p.a.) and in the form of a 75 wt % aqueous solution.

The process in accordance with the present invention is carried out using means and equipment known to a person of ordinary skill in the art. It can be carried out either batchwise or in a continuous reactor operation. Preferably, a reactor equipped with a turbo stirrer is used.

The oxidation reaction is started after the introduction of oxygen into a reaction mixture containing a compound of formula II and a catalyst, typically by starting the stirrer of the reactor (see below).

The concentration of the starting material, i.e. the ethoxylated quaternary ammonium compound of formula II, in the reaction mixture before commencing the oxidation reaction according to the present invention can vary within a wide range, typically from 5 to 75 wt %, based on the total weight of the reaction mixture. In the case of choline chloride a starting concentration in the range of 10 to 45 wt % is preferred.

The oxidation process according to the present invention must be carried out under alkaline conditions, i.e. at a pH greater than 7. This typically is achieved by adding an (earth) alkali metal hydroxide or an aqueous solution thereof to the reaction mixture, although other bases like triethylamine, trimethylamine, and sodium carbonate may be used as well. The use of an alkali metal hydroxide such as sodium hydroxide is preferred, and the invention will be described further with respect to the use of this base. As a result of using an alkali metal hydroxide and a salt of formula II an alkali metal salt, e.g., sodium chloride, is obtained as a by-product in the invention process.

When the anion is a hydroxide ion or the anion of a weak acid such as acetate or bicarbonate, no additional base is necessary, although additional base may enhance the reaction rate. In this case no alkali metal salt is generated.

It was found that when choline hydroxide was used as the starting material, the product solution coloured and the catalyst degraded more and more after each reaction cycle. Furthermore, choline hydroxide, which has to be prepared from choline chloride via an anion-exchange reaction, is not stable in highly concentrated form. The use of choline bicarbonate also resulted in deactivation of the catalyst.

Typically, about an equimolar amount or up to 5 mole % excess of alkali metal hydroxide, based on the amount of ethoxylated quaternary ammonium compound of formula II, is used in the invention process. However, depending on the type of anion as explained above or on the application in which the product of the process of the invention is to be used, it may be desirable to use a less than equimolar amount of base.

In the case of choline chloride being used as the starting material, the use of less than equimolar amount of sodium hydroxide results in the formation of mixtures of choline chloride, betaine, and sodium chloride which are suitable for use as an animal feed per se. Preferably, an amount of from 0.85 to 0.95 mole of alkali metal hydroxide per mole of choline chloride is used in the invention process. As a result, the reaction does not proceed to complete conversion but stops at about 90% choline conversion. It was found that under these conditions the catalyst stability/recyclability improved. Any mixture of choline chloride, betaine, and sodium chloride may then be obtained by adding a suitable amount of choline chloride to the reaction product with a choline conversion of about 90%.

The alkali metal hydroxide may be added all at once before the start of the reaction or it may be added in portions (see below).

Preferably, the invention process is carried out at a pH in the range of from 10 to 14, more preferably 11 to 14, most preferably 12 to 13.5.

In a preferred embodiment of the invention process so much of the alkali metal hydroxide is added to the reaction mixture before the start of the oxidation reaction that a pH in the range of from 12 to 13.5 is obtained, while the remainder of the base is added after starting the oxidation reaction by the introduction of oxygen into the reaction mixture and stirring while keeping the pH constant at that value.

In the process according to the present invention oxygen or an oxygen-containing gas is used. It is typically carried out at ambient pressure in an atmosphere of pure oxygen, i.e. at a partial oxygen pressure of 1 bara ($10^5$ Pa absolute pressure). To achieve this, the air in the reactor head space is replaced by oxygen and the oxidation reaction is started by starting the stirrer. However, the invention process may be carried out at lower (e.g. 0.2 bara or $2\times10^4$ Pa) or higher (e.g. 10 bara or $10^5$ Pa) partial oxygen pressures if desired. The oxygen may also be mixed with nitrogen or air.

In a preferred embodiment of the invention process the partial oxygen pressure is kept constant, in particular at a value of about 1 bara ($10^5$ Pa).

Preferably, the oxygen concentration in the reaction mixture, i.e. the aqueous phase, is kept below 100 ppm, more preferably below 50 ppm, most preferably below 25 ppm during the entire reaction. One way of adjusting the oxygen concentration is by controlling the rate of stirring. Another way of adjusting the oxygen concentration is by diluting the oxygen with nitrogen. Methods for determining the oxygen concentration in reaction mixtures are known to the person skilled in the art.

It was found that when the pH of the reaction mixture was kept constant at a value in the range of from 12 to 13.5 by dosing alkali metal hydroxide and at the same time controlling the oxygen concentration in the reaction mixture by keeping the partial oxygen pressure at a constant value of 1 bara ($10^5$ Pa) and selecting an appropriate stirring speed so as to keep the oxygen concentration in the reaction mixture below 100 ppm, the catalyst stability and hence the recyclability improved.

The catalyst stability is determined by calculating the Pt loss in ppm per reaction cycle (i.e. batch) (see Examples). In the aforementioned way, Pt losses of less than 1.5 ppm per reaction cycle can be obtained.

The supported and promoted platinum catalyst used in the process according to the present invention is known in the art, see, e.g., C. Brönnimann et al., *J. Catal.*, 150 (1994) 199–211 and A. Abbadi and H. van Bekkum, *Appl. Catal.* 124 (1995) 409–417, and typically consists of a noble metal, a support which is stable and inert, and a promoter metal. These catalysts are commercially available, e.g., from Degussa, but if desired may also be prepared by the person skilled in the art as described below.

A particularly suitable support is carbon. Suitable promoter metals include Bi, Cd, and Pb with Bi being preferred. A particularly preferred catalyst for use in the invention process is a Pt/Bi/C catalyst. This catalyst can be re-used many times and the filtered catalyst is immediately ready for use in a new oxidation reaction cycle.

If desired, the catalyst can be premanufactured or it can be formed in situ before starting the oxidation reaction.

In the former embodiment, the promoter metal in the form of a suitable oxide or salt thereof is dissolved, e.g., bismuth (III) oxide in aqueous hydrochloric acid or bismuth(III) nitrate in aqueous nitric acid, mixed with an aqueous dispersion of a supported Pt catalyst, e.g. 5% Pt on carbon, and the promoter metal is precipitated onto the supported Pt catalyst by the addition of an aqueous sodium hydroxide solution. The supported and promoted Pt catalyst is then isolated by filtration and washing with water.

In the latter embodiment, the promoter metal in the form of a suitable oxide or salt thereof, e.g., bismuth(III) oxide, bismuth(III) chloride or bismuth(III) nitrate, is added to the reaction mixture separately from the supported Pt catalyst, e.g. 5% Pt on carbon, before the start of the reaction. The supported and promoted Pt catalyst is then formed in situ (see the Examples below).

The amount of the supported and promoted Pt catalyst to be used in the invention process typically is in the range of 0.5 to 10 wt %, preferably 1 to 9 wt %, based on the total weight of the reaction mixture, i.e. the total weight of all reaction ingredients.

The Pt to promoter metal molar ratio in the catalyst typically is in the range of 3:1 to 1:3, preferably 2:1 to 1:2, more preferably about 1:1.

The supported and promoted Pt catalyst typically contains from 1 to 20 wt %, preferably 5 to 10 wt % of Pt and from 1 to 20 wt %, preferably 5 to 15 wt % of promoter metal, based on the total weight of the catalyst.

Typically, the compound of formula II to Pt molar ratio is in the range of from 100 to 1100, preferably 200 to 500, more preferably 200 to 350.

The invention process is preferably carried out at a temperature of from 20 to 60° C., more preferably 20 to 50° C., most preferably 20 to 40° C.

Typically, the reaction time is in the order of 0.2 to 3 h.

It was found that an optimum had to be determined for the invention process with respect to catalyst deactivation on the one hand and the space-time yield on the other hand. This optimum can easily be determined by one of ordinary skill in the art via routine experimentation using the above description of the present invention and the examples below as a guidance. Important parameters for the invention process are the oxygen concentration in the reaction mixture and the mass transfer rate. These parameters can be controlled by means of the partial oxygen pressure, catalyst concentration, pH, stirring speed, and reaction temperature.

The present invention is illustrated by the following examples.

EXAMPLE 1

To a glass reactor were added 94.3 g of a 75 wt % aqueous choline chloride (CC) solution[1] followed by 336.0 g of deionized water, 20.6 g of NaOH, and 10.6 g of a Pt/Bi/C catalyst[2] with a solids content of 45.1% (ex Degussa). In this way, a solution having a CC concentration of 15.1 wt %, a molar ratio of choline to Pt of 408, and a pH of 13.4 was obtained.

Subsequently, after establishing a partial $O_2$ pressure of 1 bara ($10^5$ Pa), mixing was started. Within 5 min the temperature of the reaction mixture had increased to 35° C. and it was kept constant at this value until the reaction was stopped after 24 min. The oxygen concentration remained well below 100 ppm. A CC conversion of 100% and a betaine selectivity of 99% were obtained as determined by HPLC analysis. A space-time yield of 327.7 g betaine per liter per hour was calculated.

After it had been used in 4 reaction cycles, a mean Pt loss of 1.2 ppm per cycle was calculated for the catalyst.

[1]Analysis showed that the actual content of choline chloride was 74 wt %.

[2]The Pt/Bi/C catalyst was bought from Degussa in the form of a wet cake (i.e. CF 196xRAW) and contained 5% Pt and 5% Bi and was used as such. The solids content is dependent on the catalyst batch.

EXAMPLE 2

To a glass reactor were added 243 g of a 75 wt % aqueous choline chloride (CC) solution followed by 104.1 g of deionized water, 9.4 g of an aqueous 33 wt % NaOH solution, and 44.8 g of a Pt/Bi/C catalyst with a solids content of 38.2% (ex Degussa) (see the notes to Example 1). In this way, a solution with a CC concentration of 44.8 wt %, a molar ratio of choline to Pt of 294, and a pH of 12.8 was obtained.

Subsequently, after the establishing of a partial $O_2$ pressure of 1 bara ($10^5$ Pa), mixing was started simultaneously with dosing of a further 131.1 g of a 33 wt % aqueous NaOH solution. Within 15 min the temperature of the reaction mixture had increased to 35° C., and it was kept constant at this value until the reaction was stopped. The NaOH was dosed at such a rate that the pH of the reaction mixture was kept constant at a value of 12.8. The oxygen concentration remained well below 100 ppm. After a period of time of 162 min, 100% NaOH conversion corresponding to 87% CC conversion and a betaine selectivity of 100% were obtained as determined by HPLC analysis. A space-time yield of 92.4 g betaine per liter per hour was calculated.

After it had been used in 150 reaction cycles, a mean Pt loss of 1.2 ppm per cycle was calculated for the catalyst.

EXAMPLE 3

To a glass reactor were added 183 g of a 75 wt % aqueous choline chloride (CC) solution followed by 147.4 g of deionized water, 9.0 g of an aqueous 33 wt % NaOH solution, and 27 g of a Pt/Bi/C catalyst with a solids content of 38.2% (ex Degussa) (see the notes to Example 1). In this way, a solution with a CC concentration of 28.3 wt %, a molar ratio of choline to Pt of 367, and a pH of 12.0 was obtained.

Subsequently, after the establishing of a partial $O_2$ pressure of 1 bara ($10^5$ Pa), mixing was started simultaneously with dosing of a further 111.6 g of a 33 wt % aqueous NaOH solution. The temperature of the reaction mixture went up to 35° C., and it was kept constant at this value until the reaction was stopped after 79 min. The NaOH was dosed at such a rate that the pH was kept constant at a value of 12. The oxygen concentration remained well below 100 ppm. A CC conversion of 100% and a betaine selectivity of 99% were obtained. A space-time yield of 178.7 g betaine per liter per hour was calculated.

After it had been used in 4 reaction cycles, a mean Pt loss of 1.1 ppm per cycle was calculated for the catalyst.

EXAMPLE 4

Following the same procedure as described in Example 1, but using 183 g of the CC solution (i.e. a molar ratio of choline to Pt of 792), adding 228.5 g of water and 40 g of NaOH, and carrying out the reaction at 50° C. for a period of time of 126 min, a CC conversion of 98.4% and a betaine selectivity of 96.1% were obtained. The space-time yield was calculated to be 109.9 g betaine per liter per hour. The Pt loss was calculated to be 4.3 ppm.

EXAMPLE 5

Following the same procedure as described in Example 1, but using 5 g of the Pt/Bi/C catalyst (i.e. a molar ratio of choline to Pt of 865) and carrying out the reaction at a partial oxygen pressure of 2 bara ($2\times10^5$ Pa) for a period of time of 48 min, a CC conversion of 85.2% and a betaine selectivity of 95.8% were obtained. The space-time yield was calculated to be 136.8 g betaine per liter per hour. The Pt loss was calculated to be 1.6 ppm.

EXAMPLE 6

To a glass reactor were added 25.4 g of choline chloride (CC), 7.4 g of NaOH, 7.14 9 of wet 5% Pt/C with a solids content of 50.4%, 130 g of water, and 0.444 g of bismuth(III) nitrate pentahydrate (i.e. a choline to Pt molar ratio of 195.5 and a Pt to Bi molar ratio of 1.0). The oxidation reaction was carried out at a partial oxygen pressure of 1 bara ($10^5$ Pa). The oxygen concentration remained well below 100 ppm.

After a reaction time of 60 min at 38° C., a CC conversion of 100%, a betaine selectivity of 99.0%, and a space-time yield of 139.4 g betaine per liter per hour were obtained. The Pt loss was calculated to be 0.56 ppm.

EXAMPLE 7

To a 0.5 l glass reactor equipped with a turbo stirrer containing a mixture of 29.4 g (0.1 mole) of N-dodecyl N,N-dimethyl N-(2-hydroxyethyl) ammonium chloride and 225 ml of water were added 4.2 9 (0,105 mole) of sodium hydroxide. Subsequently, 2.5 g of a Pt/Bi/C catalyst (ex Degussa, see the note to Example 1) with a solids content of 38.2% was added to the solution. In this way, a solution having an ammonium chloride concentration of 11.1 wt %, a molar ratio of ammonium compound to Pt of 156, and a pH of 12.8 was obtained.

The reaction mixture was contacted with oxygen, which was introduced into the gas phase of the reactor via a gas burette, by means of efficient stirring. The reaction temperature was kept between 25 and 45° C. The oxygen concentration remained well below 100 ppm.

After 19 min the oxygen consumption came practically to a stop and the reaction was concluded. The reaction solution was separated from the catalyst via a filter candle and the solution was freeze-dried. $^{13}$C-NMR analysis of the product showed that the conversion of the N-dodecyl-N,N-dimethyl N-(2-hydroxyethyl) ammonium chloride was 95% and the yield of N-dodecyl betaine was 93%. Betaine selectivity was 98% and a space-time yield of 312 g betaine per liter per hour was calculated. The Pt loss was not measured.

EXAMPLE 8

Following the same procedure as described in Example 7, but using 0.1 mole of N-coco N,N-dimethyl N-(2-hydroxyethyl) ammonium chloride and after a reaction time of 17 min, N-coco betaine in a yield of 94% according to $^{13}$C-NMR analysis was obtained. Betaine selectivity was 98% and a space-time yield of 390 g betaine per liter per hour was calculated. The Pt loss was not measured.

COMPARATIVE EXAMPLE A

Example 5 of U.S. Pat. No. 5,895,823 shows that the reaction of choline hydroxide with oxygen in the presence of a 5% Pd/C catalyst (the molar ratio of choline to Pd being 76) for 5.5 hours at 78° C. results in a choline conversion of 89% and a betaine selectivity of 87%.

A space-time yield of 65.4 g betaine per liter per hour was calculated.

COMPARATIVE EXAMPLE B

When the oxidation reaction of CC was carried out in the presence of 5% Pt/C as the catalyst at 35° C., a choline chloride concentration of 14.8 wt % and a choline to Pt molar ratio of 195.5, a Pt loss of 50.4 ppm was calculated. When this catalyst was used a second time, the choline conversion had dropped from 95% to 67.5% and the Pt loss had increased to 57.6 ppm.

COMPARATIVE EXAMPLE C

When Example 2 was repeated using a Pd/Bi/C catalyst, obtained by contacting a 5.2% Pd/C catalyst with bismuth (III) nitrate pentahydrate at a molar ratio of Pd to Bi of 1:1 according to the procedure described in Example 6, no choline conversion was observed at either 35° C. or 50° C.

As shown by the Examples in accordance with the present invention, the invention process in its preferred embodiments provides a higher choline conversion, a higher betaine selectivity, a higher space-time yield, and a shorter reaction time at a higher molar ratio of choline to Pt and at a lower reaction temperature as compared to the prior art process. In addition, the catalyst employed in accordance with the present invention process can be re-used many times without losing its stability in terms of loss of Pt.

What is claimed is:

1. A process for preparing betaines of formula I:

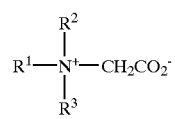

I wherein $R^1$ represent a $C_1$–$C_{24}$ hydrocarbon group, and $R^2$ and $R^3$ independently represent a $C_1$–$C_3$ hydrocarbon group, comprising reacting an aqueous solution of an ethoxylated quaternary ammonium compound of formula II:

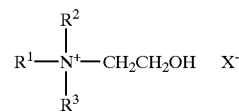

II wherein $R^1$, $R^2$, and $R^3$ have the same meaning as described above and

X$^-$ represents a suitable anion, with oxygen or an oxygen-containing gas under alkaline conditions in the presence of a supported and metal-promoted Pt catalyst at a temperature ranging from room temperature to 70° C., and wherein the pH of the reaction mixture is kept constant at a value in the range of from 12 to 13.5.

2. The process according to claim 1 wherein the catalyst is a Bi-promoted catalyst.

3. The process according to claim 1 wherein the reaction temperature is in the range of from 20 to 60° C.

4. The process according to claim 1 wherein the compound of formula II to Pt molar ratio is in the range of from 100 to 1100.

5. The process according to claim 1 wherein $R^1$ represents a $C_1$–$C_{24}$ hydrocarbon group and $R^2$ and $R^3$ represent methyl groups.

6. The process according to claim 5 wherein $R^1$–$R^3$ represent methyl groups.

7. The process according to any one of claims 1–6 wherein X$^-$ represents a halide ion.

8. A process according to any one of claims 1–7, characterized in that the partial oxygen pressure is kept constant at a value of 1 bara ($10^5$ Pa).

9. A process according to any one of claims 1–7 and 8, characterized in that the oxygen concentration in the reaction mixture is kept below 100 ppm.

* * * * *